US012502296B1

(12) United States Patent
Jablonka et al.

(10) Patent No.: US 12,502,296 B1
(45) Date of Patent: Dec. 23, 2025

(54) ANKLE BRACE WITH ACHILLES TENDON SUPPORT

(71) Applicant: WEBER ORTHOPEDIC, L.P., Santa Paula, CA (US)

(72) Inventors: James M. Jablonka, Wethersfield, CT (US); James Buckhout, Keller, TX (US); Kelly Nolan, Trophy Club, TX (US)

(73) Assignee: WEBER ORTHOPEDIC, L.P., DFW Airport, TX (US)

( * ) Notice: Subject to any disclaimer, the term of this patent is extended or adjusted under 35 U.S.C. 154(b) by 268 days.

(21) Appl. No.: 18/389,539

(22) Filed: Nov. 14, 2023

Related U.S. Application Data

(60) Provisional application No. 63/425,944, filed on Nov. 16, 2022.

(51) Int. Cl.
*A61F 5/01* (2006.01)

(52) U.S. Cl.
CPC .................................. *A61F 5/0111* (2013.01)

(58) Field of Classification Search
CPC .... A61F 5/0111; A61F 5/0113; A61F 5/0127; A61F 5/32; A43B 7/20; A41D 13/05; A41D 13/06
See application file for complete search history.

(56) References Cited

U.S. PATENT DOCUMENTS

| | | | | |
|---|---|---|---|---|
| 5,000,195 | A * | 3/1991 | Neal | A61F 5/0111 602/27 |
| 5,135,473 | A | 8/1992 | Epler et al. | |
| 5,464,384 | A | 11/1995 | Cromartie | |
| 6,117,098 | A * | 9/2000 | Weber | A61F 13/066 602/65 |
| 7,361,154 | B2 | 4/2008 | Jablonka et al. | |
| 7,908,771 | B2 * | 3/2011 | Foxen | A43B 5/18 602/65 |
| 8,454,545 | B1 | 6/2013 | Weber et al. | |
| 8,821,427 | B1 * | 9/2014 | Weber | A61F 5/0111 602/23 |
| 9,357,804 | B2 * | 6/2016 | Bue, Jr. | A41D 13/05 |
| 9,421,117 | B1 | 8/2016 | Hames | |
| 9,788,987 | B2 | 10/2017 | Vollbrecht et al. | |
| 11,344,422 | B2 * | 5/2022 | Maale | A61F 2/4081 |
| 11,571,318 | B1 * | 2/2023 | Kuehl | A61F 5/0111 |
| 2007/0049857 | A1 * | 3/2007 | Quinn | A61F 5/0111 602/27 |

(Continued)

*Primary Examiner* — Kari K Rodriquez
(74) *Attorney, Agent, or Firm* — Paul Y. Feng; ONE LLP

(57) ABSTRACT

An orthopedic ankle brace allowing rear entry through an open back, enclosed by a back panel with tendon buttresses that pinch the Achilles tendon between the buttresses. The brace includes a gauntlet having a front panel with a forefoot opening underneath, a bottom integrated to opposed side panels, an open top, and an open back. A lace closure system cinches the front panel and side panels together. The back panel has an elastic center section separating two wings that attach to the gauntlet. Two tendon buttresses separated by a gap are disposed inside the back panel, and when the back panel is attached to the gauntlet, the gap receives the Achilles tendon. A tendon strap, overlying the tendon buttresses, when tightened squeezes the tendon buttresses together against the Achilles tendon held therebetween.

20 Claims, 6 Drawing Sheets

(56) References Cited

U.S. PATENT DOCUMENTS

| | | | | |
|---|---|---|---|---|
| 2009/0112140 | A1* | 4/2009 | Gaylord | A61F 5/0111<br>602/27 |
| 2013/0326799 | A1* | 12/2013 | Bue, Jr. | A61F 5/0111<br>2/455 |
| 2024/0366411 | A1* | 11/2024 | Grundmann | A61F 5/30 |
| 2025/0134688 | A1* | 5/2025 | Madden | A61F 5/0111 |

* cited by examiner

ANKLE BRACE WITH ACHILLES TENDON SUPPORT

CROSS-REFERENCE TO RELATED APPLICATIONS

This non-provisional application claims benefit of priority from U.S. provisional application No. 63/425,944, filed Nov. 16, 2022, the contents of which are hereby incorporated by reference.

FIELD OF THE INVENTION

The present invention relates to an orthopedic brace. More particularly, the present invention relates to an ankle brace.

BACKGROUND

Orthopedic joint supports are used for the treatment and post-op rehabilitation of a patient's injured musculoskeletal system. Such pain or injury commonly arise from arthritis, bone fractures, sports injuries, soft tissue tears, etc. Orthopedic joint supports are used for the treatment and post-op rehabilitation of a patient's injured musculoskeletal system. Such pain necessitates either invasive or non-invasive treatment, and orthopedic joint supports are used during or after such treatment.

SUMMARY OF THE INVENTION

The present invention is directed to an orthopedic ankle brace. The ankle brace in a preferred embodiment comprises a gauntlet having two opposed side panels integrated by a bottom, and a front panel or tongue elastically joined to the two side panels, wherein the gauntlet includes an open top, an open back, and a forefoot opening beneath the front panel. The gauntlet uses a lace closure system binding the front panel to the two side panels. Optional semi-rigid stays are disposed inside each side panel. Hook-and-loop fasteners are disposed on the preferably outside surface of the side panels. The ankle brace includes a detachable back panel constructed from two wings separated by an elastic center section, wherein each wing includes hook-and-loop fasteners that attach to the gauntlet side panels.

The preferred embodiment ankle brace further includes at least two non-inflatable, compressible and deformable tendon buttresses arranged generally vertically and parallel to each other separated by a gap therebetween and disposed on the back panel. The gap has a width and a depth sufficient to receive the Achilles tendon at least partially therein while also minimizing posterior pressure received from the back panel pushing against the Achilles tendon.

A tendon strap is disposed on the exterior of the back panel and anchored at the two wings while overlying the tendon buttresses. When the user or clinician cinches the tendon strap, the strap compresses and deforms (i.e., flattens) the tendon buttresses, closing the gap, and squeezing or pinching the Achilles tendon between the tendon buttresses. The back panel is joined to the gauntlet via the hook-and-loop fasteners and at least partially encloses the open back of the gauntlet.

The lace closure system optionally includes a wire strand or lace passing through loop eyelets in the front panel and side panels to cinch everything together. The lace closure system may use a rotating, ratcheting spool to accumulate the wire strand for tightening the brace, with release of the ratchet and opposite rotation of the spool to loosen the wire strands. The interior of the back panel may include pockets for receiving the tendon buttresses therein, or alternatively, the tendon buttresses may be glued or attached in any manner known in the art to the interior of the back panel.

The hook-and-loop fasteners on the exterior of the side panels may have areas of UBL (Unbroken Loop) fabric and the wings include molded hook fabric for attachment to the UBL fabric. Further, the elastic center section includes a soft, elastic nylon Lycra fabric where it overlies the Achilles tendon. For comfort, the front panel and other parts of the gauntlet may include internal padding.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

The present invention is directed to an ankle brace that is effective in the treatment of Achilles Tendonitis and Sever's Disease. Achilles tendon conditions have historically been difficult to treat. It afflicts an increasing number of active children suffering from Sever's disease (heel pain resulting from increased pull by the Achilles onto the bone, because of a growth spurt), along with the classic presentation of the older athlete or individual. Heel lifts have been shown to have limited effectiveness, leaving pharmacological therapy with their unwanted side effects as a last resort. There are conventional ankle braces available that cushion the Achilles tendon by placing pads directly over or lateral to the Achilles tendon along with counterforce strapping (direct compression) directly against the Achilles tendon.

The present invention, however, utilizes a strap that incorporates a unique arrangement that supports the Achilles tendon via two adjustable tendon buttresses or pads. This structure "approximates" the Achilles tendon, because they are affixed to a strap that allows the patient the ability to adjust the tension level of those buttresses compressing on the Achilles from the medial and lateral sides, while not applying direct (and painful) pressure on the Achilles from the posterior direction.

Furthermore, the present invention ankle brace accommodates a rear entry (posteriorly) for the wearer to install his or her foot. The rear entry feature is especially beneficial when the patient with an injured and sensitive Achilles tendon does not want to experience any contact friction or pressure when applying or removing the ankle brace. A removable back panel encloses the foot inside the brace. The laces are cinched down to secure the brace to the patient's foot. The back panel can be opened to release the foot from the brace. Again, this allows easy donning of the brace as the patient slips his or her foot into the brace and closes it securing the brace on the ankle.

Figure 1:
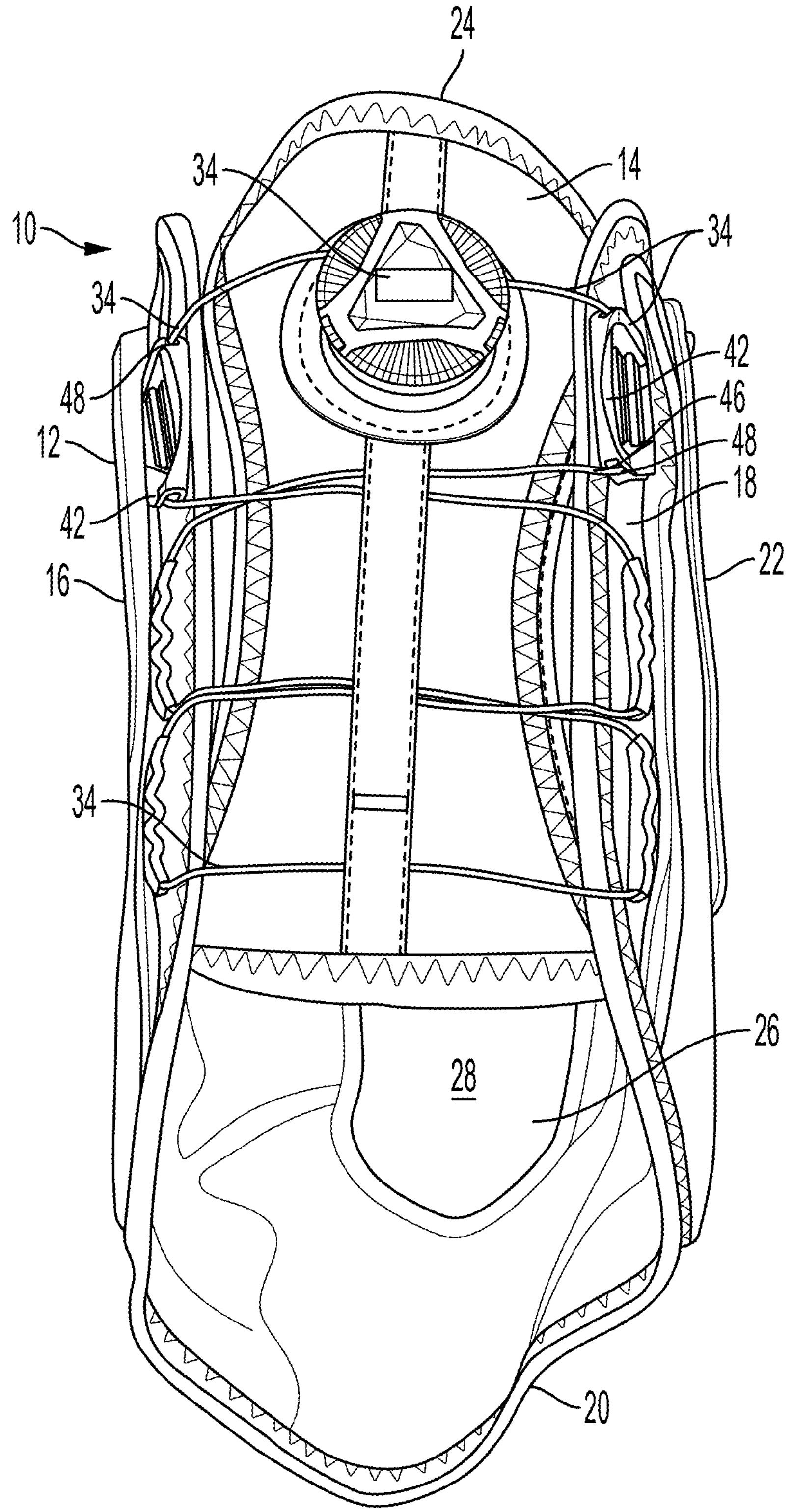
FIG. 1 is a front elevational view of a preferred embodiment ankle brace with Achilles tendon support.
Figure 2:
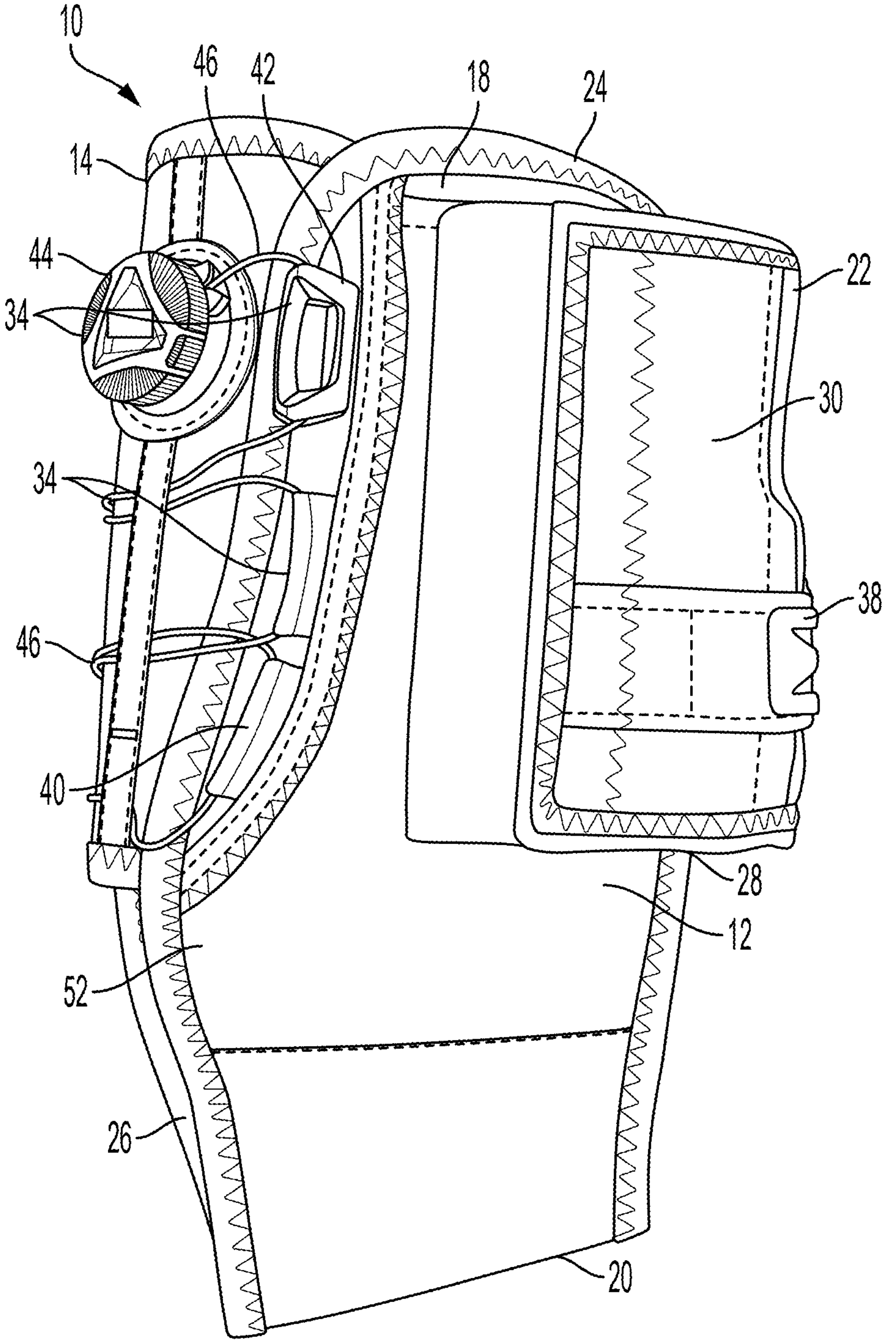
FIG. 2 is a side elevational view of the ankle brace shown in FIG. 1.
Figure 3:
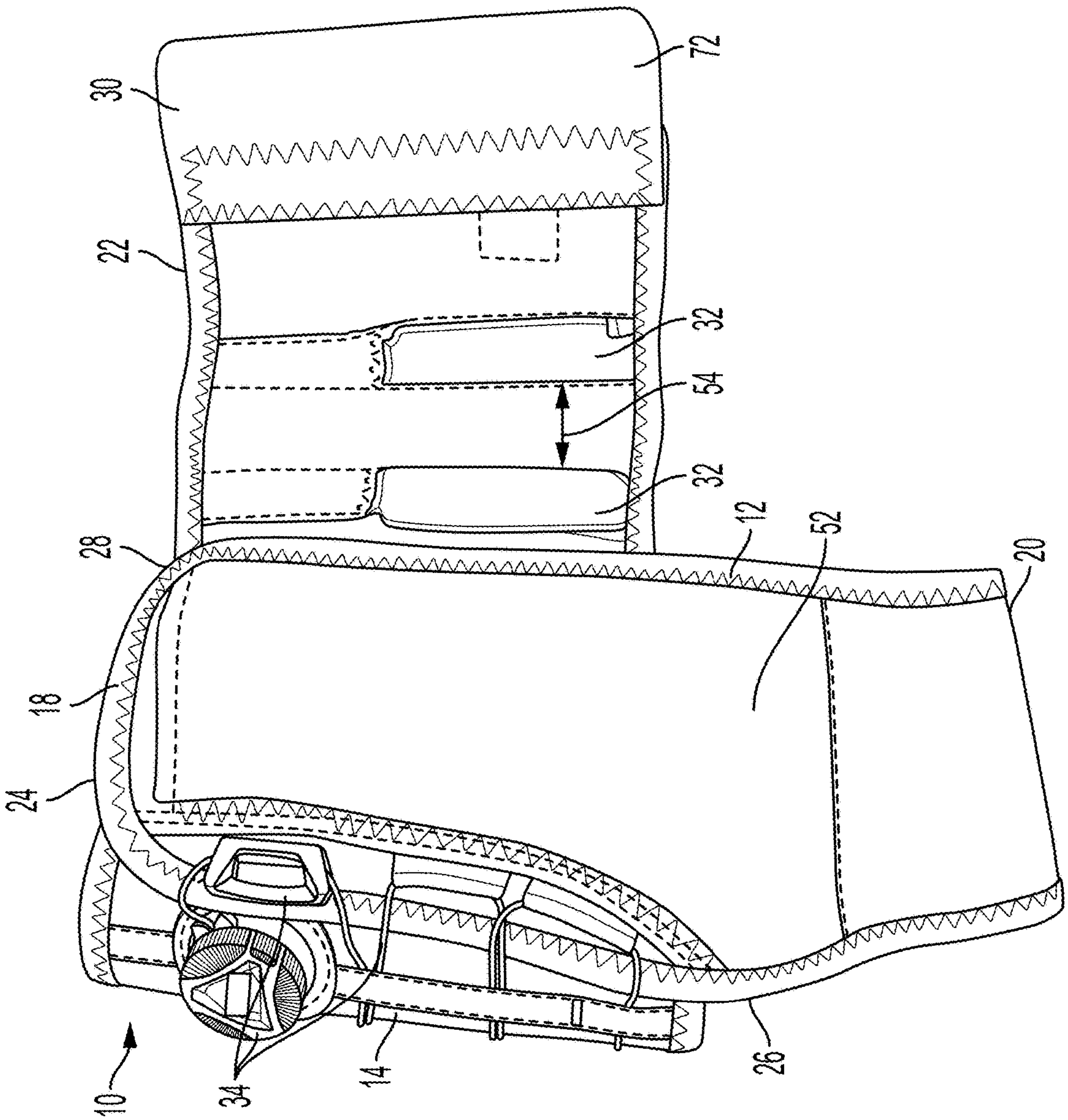
FIG. 3 is a side elevational view of the ankle brace with the back panel in the open position allowing rear entry of the wearer's foot.

FIGS. 1, 2, and 3 show a front view and side elevational views of the preferred embodiment ankle brace 10. As seen in FIG. 2, the brace 10 has an L-shaped gauntlet 12 with a back panel 22 attached to it, shown in the closed position. In contrast, FIG. 3 shows the gauntlet 12 with the back panel 22 in the open position for rear entry of the wearer's foot.

The gauntlet 12 has a front panel or tongue 14, that is elastically attached to two opposed side panels 16, 18. The side panels 16, 18 are integrated together by a bottom 20 of the gauntlet 12. Beneath the front panel 14 is an opening 26 allowing the forefoot of the wearer to pass through. The gauntlet 12 has an open top 24 to receive the wearer's lower leg, and an open back 28, closable by the removable back panel 22. There is preferably an open space beneath the back panel 22 to allow the wearer's heel to protrude through. The gauntlet 12 wraps at least part of the ankle and sides, heel, arch and instep part of the foot.

As best seen in FIGS. 1 and 2, the gauntlet 12 has a lace closure system or means 34 which may simply be shoe laces with a knot or a hooked end, or as shown here, a ratcheting twist knob/spool 44 that cinches a wire strand 46 or lace threaded through a network of loops 40 and rigid plastic D-rings 42 attached to the front panel 14 and side panels 16. The spool 44 collects the wire strand 46 wrapped around it, and turning the spool in one direction shortens and tightens the wire strand; the spool is ratcheted to prevent counter-rotation and loosening of the wire strand. Releasing the ratchet lock allows counter-rotation of the spool to loosen the wire strand. This technology is well-known in the art. The wire strand is preferably made from nylon that may be a weave, a single strand, twisted fibers, or any combination thereof.

Each D-ring 42 includes a groove or eyelet 48 (FIGS. 1, 7) through which the wire strand 46 slidably passes. The wire strand 46 is wound around the spool and twisting clockwise or counterclockwise on the twist knob 44 shortens or lengthens, respectively, the wire strand 46. This action cinches or releases tension on the wire strand 46, which affects the tightness of the front panel 14, side panels 16, 18, closed back panel 22, and the gauntlet in general on the wearer's ankle. As the knob 44 is twisted clockwise to increase tension, an internal lock or ratchet prevents that knob from counter-clockwise rotation and inadvertently releasing that tension.

Other closure means are contemplated, such as a simple shoe lace passing through eyelets or loops; straps that attach to buckles, hooks, D-rings, hook-and-loop fasteners (e.g., VELCRO®), pushbutton snaps; or one or more zippers. Any combination of closure systems may be employed in the ankle brace. The wire strand or lace 46 may be elastic or inelastic.

Figure 4:
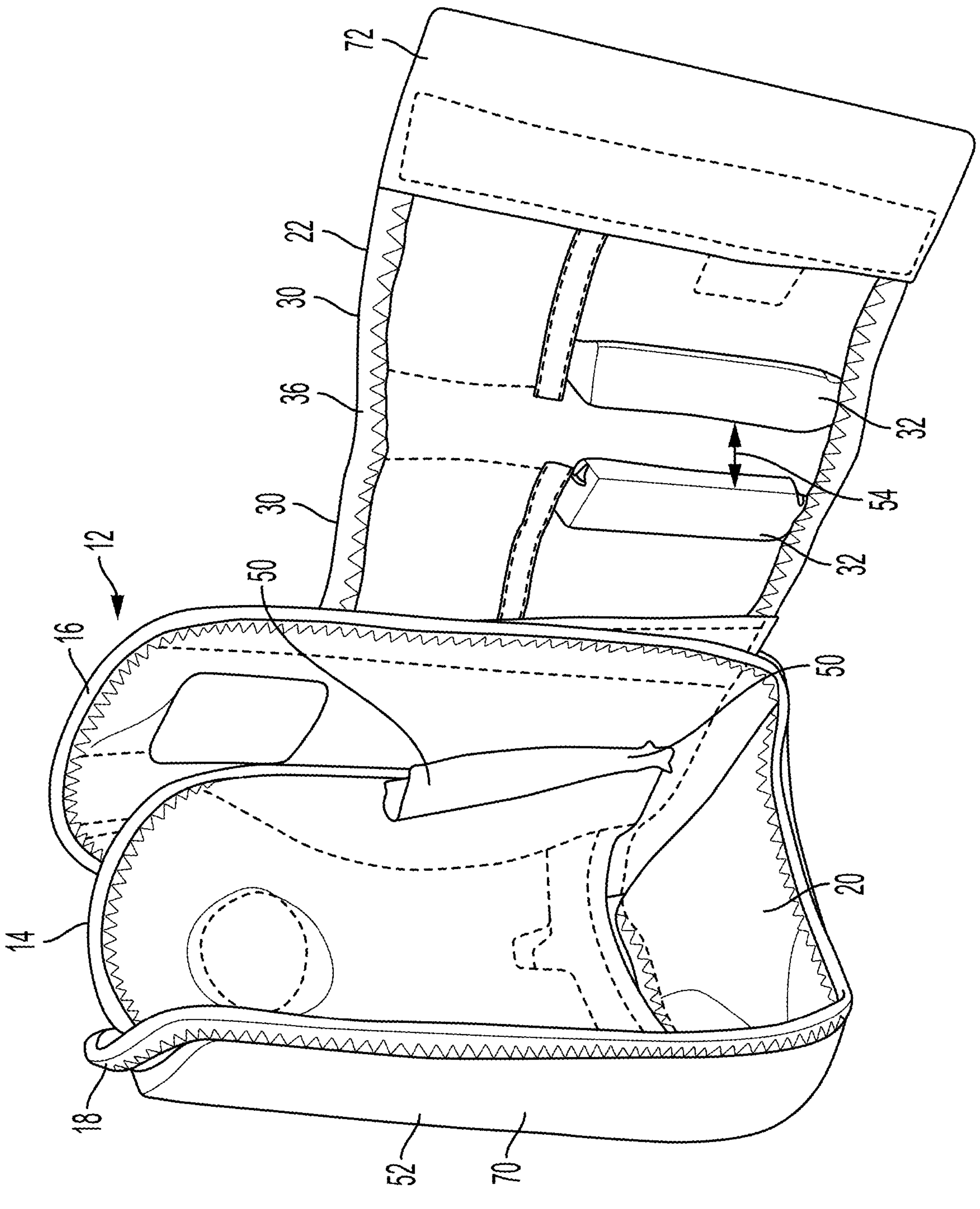
FIG. 4 is a three-quarter rear view of the ankle brace showing the interior of the gauntlet.

As seen in FIG. 4, the open back 28 enables the wearer to easily apply the ankle brace 10, without encountering painful direct pressure or friction to the injured and therefore sensitive Achilles tendon. Attached to the gauntlet 12 at the open posterior is the back panel 22 seen in FIGS. 2-4 that preferably uses hook-and-loop fasteners 72 (FIGS. 3, 5) to adjustably join the two components together. Other attachment means in addition to or in combination with the hook-and-loop fasteners 72 are contemplated, such as straps, hooks and eyelets, zippers, button snaps, D-rings, and the like.

Figure 5:
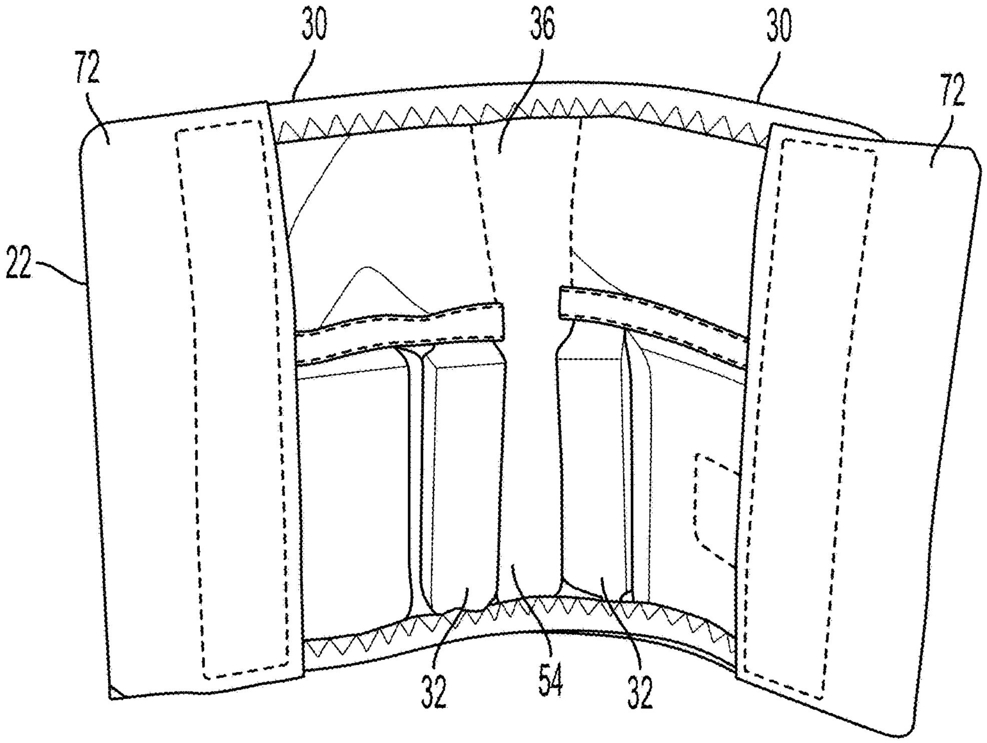
FIG. 5 shows the interior of the back panel.
Figure 6:
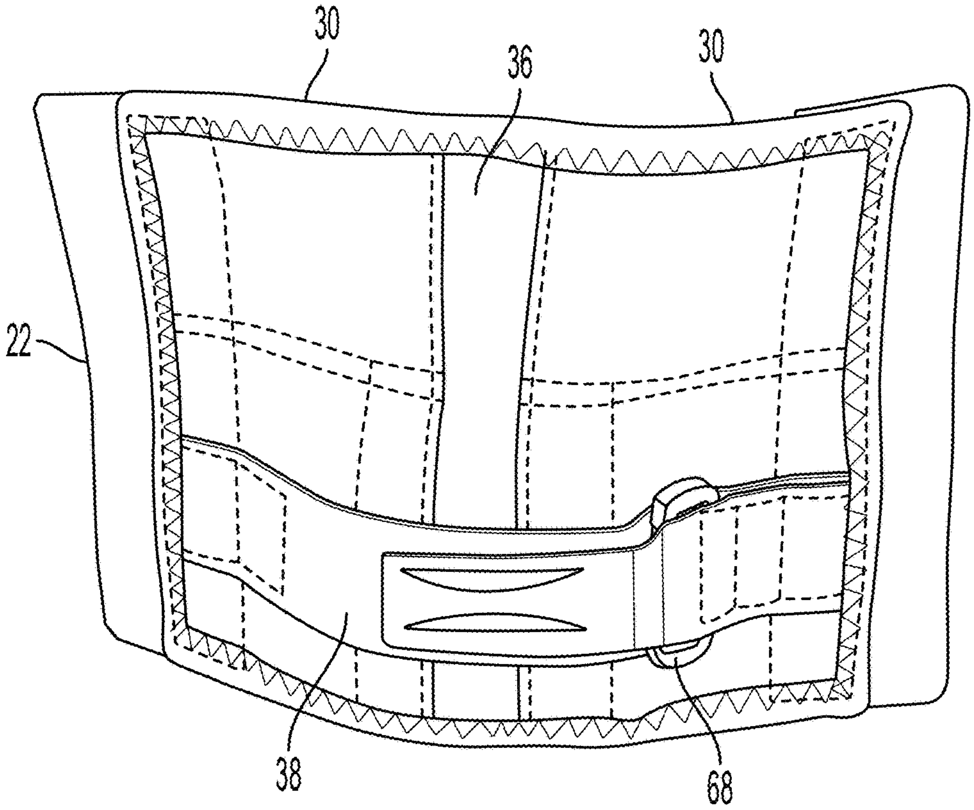
FIG. 6 shows the exterior of the back panel.

FIG. 4 shows the interior of the gauntlet 12 with the back panel 16 swung to the open position. As seen in FIGS. 5 and 6, the back panel 16 may be fully detached from the gauntlet 12 if needed, because hook-and-loop fasteners 72 are used to hold the two components together. Fabric used in the gauntlet 12 include nylon or the like and may further include internal padding to improve the wearer's comfort and the brace's overall structural integrity.

Figure 9:
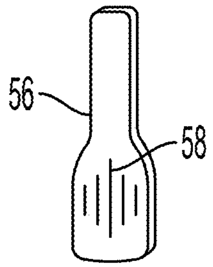
FIG. 9 shows a stay.

The side panels 16, 18 may each include internal pockets located at area 70 (FIG. 4) to hold one or more stays/stiffeners 56 shown in FIG. 9. The stay 56 preferably has slits 58 arranged longitudinally to allow torsional flexibility to mold to the shape of the ankle. The wine bottle profile of the stay 56 helps retain longitudinal bending stiffness to better hold the shape of the brace. The stays 56 are made from a rigid polymer, but aluminum, rubber, and the like are also contemplated. Also, the semi-rigid plastic stays 56 help add a little medial and lateral support as well as helping keep the brace 10 from "accordioning" or flopping down. These structures are used for improved support to the ankle.

In the preferred embodiment, the gauntlet 12 has been cut down in size and girth to remove any materials or structures that might enter the wearer's mid-foot. As seen in FIGS. 1, 2, the sleek, low profile allows the user to wear the brace 10 even with dress shoes. The front panel or "tongue" 14 (as in a shoe) of the gauntlet 12 is built from more rigid materials to allow various closure system such as a twist-knob-to-tighten lacing system 34 (FIGS. 1, 2) or other lacing designs.

As depicted in FIGS. 2-4, the exterior surfaces of the gauntlet 12 are preferably covered with UBL (Unbroken Loop) patches or like hook-and-loop fasteners. The UBL is intended to receive patches with complementary hooks positioned on the wings 30 of the back panel 22. Areas within the interior of gauntlet 12 and back panel 16 may be lined with felt or soft fabric. An elastic fabric swatch 50 (FIG. 4) is used to connect the front panel 14 to the side panels 18 so the size of the ankle brace 10 may easily be expanded or reduced according to wearer's ankle size. The elastic fabric swatch 50 with the lacing closure system 34 together help maintain the structural integrity of the front panel and two side panels when the ankle brace 10 is opened. The elastic fabric swatch 50 with the closure system 34 further enables the ankle brace 10 to dramatically increase or decrease internal space to enhance its applicability to wearers of all ankle sizes.

As seen in FIGS. 3-5, and 8 the back panel 22 preferably includes at least two tendon buttresses 32, that are contained or hidden inside respective pockets stitched to the interior surface. There are preferably two, but there may be more than that number based on physical therapy or rehab requirements. The pockets cover the buttresses 32 with a soft, smooth fabric that does not irritate the skin. Alternatively, the pockets may be omitted with the buttresses glued, stitched, or attached to the interior by any means known in the art.

As seen in FIGS. 3-5, the two tendon buttresses 32 are arranged generally parallel to each other and spaced apart by a gap 54. This arrangement allows the tendon buttresses 32 to abut and compress the injured and sensitive Achilles tendon from the medial and lateral sides (pinching action). From empirical testing, their tendon contact surfaces should be smooth, enabled by their overall shape. There should also be some rigidity to resist longitudinal bending, achieved by the solid core, to help stabilize the Achilles tendon's large girth.

Figure 8:
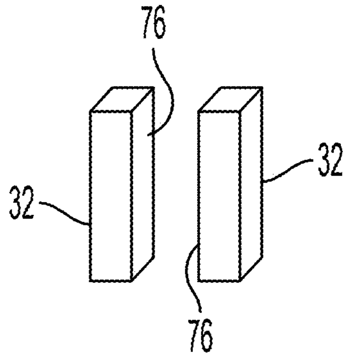
FIG. 8 shows the preferred embodiment tendon buttresses.
Figure 10A:
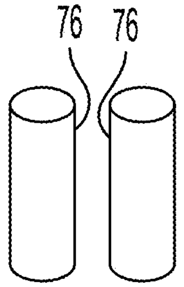
FIGS. 10A, 10B, and 10C show alternative embodiment tendon buttresses having an ovoid shape, a rhomboid shape, and a rolled tubular shape, respectively.
Figure 10B:
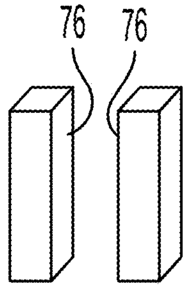
Figure 10C:
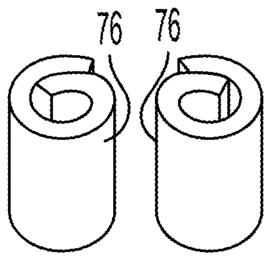

As seen in FIGS. 3, 4, and 8, the tendon buttresses 32 preferably have a blocky rectangular shape. Each tendon buttress 32 is preferably non-inflatable, or optionally, may have a solid core, and is preferably made from a resilient, compressible and deformable elastomeric material such as NEOPRENE® rubber and the like. In alternative embodiments, the tendon buttresses may have an ovoid shape, a rhomboid shape, and a tubular shape with a hollow center made by, e.g., a rolled sheet of elastic or resilient material, as seen in FIGS. 10A, 10B, and 10C, respectively.

As seen in FIGS. 8 and 10A-10C, the interior opposed surfaces 76 of the tendon buttress pairing 32 that engage the Achilles tendon therebetween are preferably blunt and smooth with no edge, seam, or sharp corners. This design is intended to firmly support the Achilles while minimizing acute pressure points that may impart pain on the sensitive tendon. The number of, size, and shape of the tendon buttresses 32 may be varied as needed to address the wearer's Achilles tendon rehab requirements and/or customized to fit the anatomy of a man, woman, adult, or child.

As best seen FIG. 6, the tendon support system in the ankle brace 10 further includes an elastic or inelastic tendon strap 38 anchored or sewn at opposite ends to the exterior of the back panel 22. Preferably, the tendon strap 38 is inelastic for the most direct and precise control of pressure applied to the ankle area. The tendon strap 38 has a free end that loops through a D-ring 68 and attaches, via hook-and-loop fasteners, to itself. The tendon strap 38 also freely overlies the Achilles tendon and the two tendon buttresses 32. Adjusting the length of the tendon strap 38 thereby only adjusts the pressure exerted upon the two tendon buttresses 32 without applying any direct, posterior pressure on the injured and sensitive Achilles tendon. This is depicted in more detail in FIG. 7.

Figure 7:
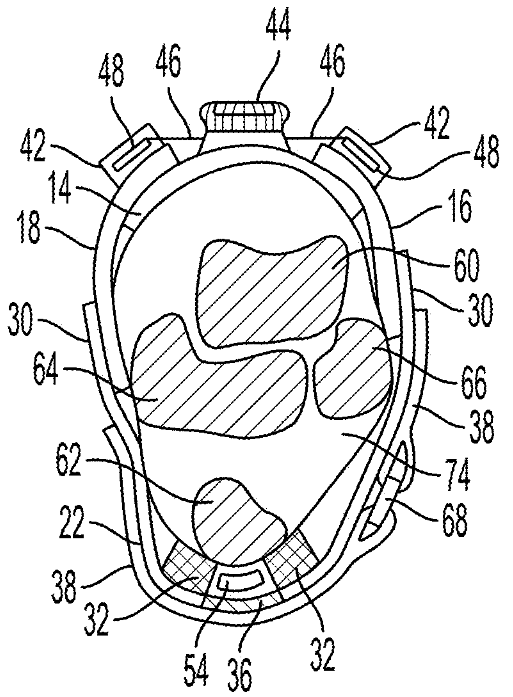
FIG. 7 is a top-looking-down, cross-sectional view of the ankle brace applied to a wearer's ankle.

FIG. 7 is a top-down, cross-sectional diagram of a wearer's ankle 74 with the ankle brace 10 applied. The tibia 64, fibula 66, and calcaneal (Achilles) tendon 62 are shown. The tendon buttresses 32 are spaced apart by the gap 54. The gap 54 has a width and a depth (loosely represented by the bold-outline rectangle in FIG. 7) chosen to accommodate the Achilles tendon 62 at least partially therein. Thus, the tendon buttresses 32 are arranged to abut the Achilles tendon 62 on the medial and lateral sides, pinching it therebetween. The depth of the gap 54 is set by the thickness of the tendon buttresses 32, which physically lift the tightened tendon strap 38 away from directly engaging the Achilles tendon 62. If there is incidental contact due to overtightening of the tendon strap 38, then the presence of the tendon buttresses resists and minimizes the posterior pressure applied by the tendon strap 38 against the wearer's Achilles tendon 62.

In addition, as the tendon strap 38 is cinched, its compressive force tends to flatten out the compressible and deformable tendon buttresses 32. By deforming and flattening the tendon buttresses 32, thus reducing its height dimension, the buttresses simultaneously expand in their lateral dimension. The effect is much like compressing a roll of kitchen paper towels; as the roll is compressed vertically and flattens out in that dimension, the roll simultaneously expands in the lateral dimension. This lateral expansion effect of the deformed buttresses 32 further helps squeeze or pinch the Achilles tendon 62 therebetween as seen in FIG. 7. The NEOPRENE® rubber selected for the tendon buttresses 32 should have the desired durometer rating to be deformable to achieve the above-described flattening effect, yet rigid enough to minimize an overtightened the tendon strap 38 from pressing against the Achilles tendon.

The preferred embodiment tendon buttress 32 has a solid core, meaning that it is non-inflatable. In contrast, an inflatable air bladder used as a tendon buttress under compression does not allow for deformation in the compressed direction while expanding at a right angle in a second direction. This is because the inflatable bladder (essentially a balloon with an inelastic envelope) has been inflated to its capacity with air, and its envelope is expanded to its dimensional limit. So under compression, the inflatable bladder cannot deform in the compressed direction or expand in a direction 90 degrees to the compressed direction because the lateral dimension has already expanded to its maximum. The typical inflatable bladder therefore does not exhibit the flattening and expanding action exhibited with the compressible and deformable neoprene buttresses 32, as established through empirical observation.

As seen in FIG. 7, the anchored tendon strap 38 is positioned so that it freely crosses over the two tendon buttresses 32 with the D-ring 68 loop lock on one side of the ankle which allows the patient to snug the tendon buttresses to approximate the Achilles tendon.

The back panel 22 includes an elastic center section 36 dividing the two wings 30 as seen in FIGS. 5-7. The elastic center section 36 is located in between the two tendon buttresses 32, which are attached to the two wings 30 of the back panel 22. When the ankle brace 10 is applied to the ankle 74, the elastic center section 36 is stretched. As a result of the stretching, a restoring force or spring-back in the center section 36 biases the two wings 30 and the tendon buttresses 32 together, which in turn helps squeeze the tendon buttresses 32 against the Achilles tendon. The center section 36 may be made from nylon, LYCRA®, SPANDEX®, polyester, latex, or like elastic material, or any combination thereof.

The back panel 22 is attached to the gauntlet 12 by hook-and-loop fasteners, so the vertical positioning of the tendon buttresses 32 relative to Achilles tendon can be adjusted. As seen in FIGS. 2, 3, the back panel 22 has preferably been cut shorter in height than the sides panels 16, 18 of the gauntlet 12 so the back panel can be moved proximally or distally on the leg so that the two tendon buttresses 32 can be positioned up or down along the Achilles where the pain is. The Achilles can be painful at its insertion point on the calcaneus (so it is moved distally) or proximally as high as the brace rests on the leg. The back panel 22 can also be flipped upside down if necessary to relocate the tendon buttress 32, but that would be in a rare case where tendonitis was very high up on the Achilles.

Advantageously, the tendon support mechanism of the present invention ankle brace 10 utilizes the relocatable back panel 22, the tendon strap 38, and the tendon buttresses 32 to adjust to and model the Achilles tendon to normalize pressure from the irritated tissue. This method of support is consistent with established clinical rationale and allows for the involved muscle to contract with increased anatomical normalcy and efficiency. The result is a comfortable ankle support that is low profile when worn, does not utilize harmful direct compression on the Achilles, and improves function with decreased pain. With this arrangement, the ankle gauntlet 12 with the attached back panel 22 offer compression of the ankle along with slight medial and lateral support to the ankle, while still permitting free plantar flexion and dorsiflexion.

Hook-and-loop fasteners 72 are preferably employed in the preferred embodiment brace 10 to allow the back panel 22 to be relocated relative to the gauntlet to accommodate different sized ankles (e.g., male vs. female, adult vs. child). This adjustability in size allows the reseller to only keep in inventory three sizes that fit both left and right leg, and XS-S, M-L, and XL-2XL. This is unique for this style of gauntlet and is all made possible by the back panel design.

No conventional ankle braces on the market allow for the easy rear entry application. This is especially useful for obese men as it is almost impossible to self-apply an ankle brace while having a large mid-section. The present invention ankle brace also utilizes dual tendon buttresses and a tendon strap to straddle and cinch them onto the Achilles without creating a counterforce. Conventional tendonitis braces and straps do not benefit from this improvement.

The current medical understanding on the process of tendonitis supports the fact that direct compression is harmful to healing and causes deterioration of the collagen of that tendon. Approximating support, which is provided by the two tendon buttresses 32 straddling either side of the Achilles tendon as in the present invention brace 10, does not create this harmful compression and promotes normal movement of the Achilles, ultimately decreasing pain and allowing for normal tissue remodeling (i.e., healing). Beyond the obese, elderly, or limited range-of-motion person's ease-of-use benefits, the rear entry aspect increases voluntary compliance by the wearer (i.e., more consistent wear of the brace) due to improved comfort for him or her.

Therefore, the tendon strap 38 acts in concert with the paired tendon buttresses 32 that flatten and pinch the injured Achilles therebetween while minimizing or eliminating direct pressure on the Achilles from the tightened tendon strap. This novel combination results in the Achilles tendon being able to function in an anatomical manner, while being supported inside the ankle brace 10 and while the wearer goes about his or her daily activities. The anatomical functioning of the injured Achilles tendon enables it to fully recover more quickly and pain free.

From the foregoing detailed description, it should be evident that there are a number of changes, adaptations and modifications of the present invention that come within the province of those skilled in the art. Features or structures of one embodiment may be combined with features or structures in another embodiment. It is intended that all such variations not departing from the spirit of the invention be considered as within the scope thereof except as limited solely by the following claims.

What is claimed is:

1. An orthopedic ankle brace, comprising:

a gauntlet having two opposed side panels integrated by a bottom, and a front panel elastically joined to the two side panels, wherein the gauntlet includes an open top, an open back, and an opening beneath the front panel;

a lace closure system binding the front panel to the two side panels;

a semi-rigid stay disposed inside each side panel;

hook-and-loop fasteners disposed on a surface of the side panels;

a back panel having an interior, two wings separated by an elastic center section, wherein each wing includes hook-and-loop fasteners that attach to the gauntlet side panels;

at least two non-inflatable, compressible and deformable tendon buttresses arranged generally vertically and parallel to each other, creating a gap therebetween having a width and depth sufficient to at least partially receive the Achilles tendon therein, wherein the tendon buttresses are disposed on the interior of the back panel;

a tendon strap disposed on the exterior of the back panel anchored at the two wings and overlying the tendon buttresses, wherein the strap includes a D-ring and a free end that loops through the D-ring and anchors on the strap, and cinching the tendon strap closes the gap and pinches the Achilles tendon between the tendon buttresses while the tendon buttresses space the tendon strap posteriorly away from the Achilles tendon; and wherein the back panel when joined to the gauntlet via the hook-and-loop fasteners at least partially encloses the open back of the gauntlet.

2. The orthopedic ankle brace of claim 1, wherein the lace closure system includes a wire strand passing through loop eyelets in the front panel and side panels.

3. The orthopedic ankle brace of claim 1, wherein the interior of the back panel includes pockets for receiving the tendon buttresses therein.

4. The orthopedic ankle brace of claim 1, wherein the tendon buttresses are glued to the interior of the back panel.

5. The orthopedic ankle brace of claim 1, wherein the exterior of the side panels include areas of UBL fabric and the wings include molded hook fabric for attachment to the UBL fabric.

6. The orthopedic ankle brace of claim 1, wherein the elastic center section includes a fabric selected from the group consisting of nylon, polyester, and latex.

7. The orthopedic ankle brace of claim 1, wherein the front panel includes internal padding.

8. The orthopedic ankle brace of claim 1, wherein each side panel includes a secondary D-ring having a tunnel therein receiving a wire strand of the lace closure system therethrough.

9. The orthopedic ankle brace of claim 1, wherein the lace closure system includes a ratcheting spool disposed on the front panel, wherein a wire strand is wound on the ratcheting spool, and turning the spool in one direction tightens the wire strand.

10. An orthopedic ankle brace, comprising:

a gauntlet having two opposed side panels integrated by a bottom, and a front panel elastically joined to the two side panels, wherein the gauntlet includes an open top, an open back, and an opening beneath the front panel;

a means for binding the front panel to the two side panels;

a semi-rigid stay disposed inside each side panel;

hook-and-loop fasteners disposed on a surface of the gauntlet;

a back panel having two wings separated by an elastic center section, wherein each wing includes hook-and-loop fasteners that attach to the surface of the gauntlet;

at least two compressible and deformable tendon buttresses arranged generally vertically and parallel to each other separated by a gap therebetween and disposed on the back panel, wherein the gap has a width and a depth sufficient to receive the Achilles tendon at least partially therein while also minimizing posterior pressure received from the back panel pushing against the Achilles tendon;

a tendon strap disposed on the exterior of the back panel anchored at the two wings and overlying the tendon buttresses, and cinching the tendon strap flattens and deforms the tendon buttresses, closing the gap, and pinching the Achilles tendon between the tendon buttresses; and wherein the back panel when joined to the gauntlet via the hook-and-loop fasteners at least partially encloses the open back of the gauntlet.

11. The orthopedic ankle brace of claim 10, wherein the means for binding the front panel to the two side panels includes a wire strand passing through loop eyelets located on the front panel and side panels.

12. The orthopedic ankle brace of claim 10, wherein the semi-rigid stay disposed inside each side panel includes a strip made from at least one of plastic, aluminum, and steel.

13. The orthopedic ankle brace of claim 10, wherein the tendon buttresses have a blocky shape with a blunt and smooth opposed surfaces that engage the Achilles tendon.

14. The orthopedic ankle brace of claim 10, wherein the center section includes an elastic fiber fabric selected from the group of fabrics consisting of nylon, polyester, and latex.

15. The orthopedic ankle brace of claim 10, wherein the tendon strap is inelastic.

16. An orthopedic ankle brace, comprising:

a gauntlet having two opposed side panels integrated to a bottom, and a front panel elastically connected to the two side panels, wherein the gauntlet includes an open top, an open back, and an opening beneath the front panel;

a means for binding the front panel to the two side panels;

a semi-rigid stay disposed inside each side panel;

hook-and-loop fasteners disposed on a surface of the side panels;

a back panel having two wings separated by an elastic center section, wherein each wing includes hook-and-loop fasteners that attach to the gauntlet side panels;

at least two compressible and deformable tendon buttresses that are non-inflatable with opposing blunt surfaces, arranged generally vertically and parallel to each other separated by a gap therebetween and disposed on the back panel, wherein the gap has a width and a depth sufficient to at least partially receive an Achilles tendon, and the blunt surfaces of the tendon buttresses to engage the Achilles tendon laterally and medially;

a tendon strap disposed on the back panel anchored at the two wings and overlying the tendon buttresses, wherein the tendon strap includes a D-ring and a free end of the strap loops through the D-ring and anchors to the strap, and cinching the tendon strap closes the gap to squeeze the Achilles tendon between the tendon buttresses; and wherein the back panel when joined to the gauntlet at least partially encloses the open back of the gauntlet.

17. The orthopedic ankle brace of claim 16, wherein the elastic center section includes spring-back to bias the tendon buttresses together against the Achilles tendon.

18. The orthopedic ankle brace of claim 16, wherein the gap depth is sufficient to minimize posterior pressure received from the cinched tendon strap against the Achilles tendon.

19. The orthopedic ankle brace of claim 16, wherein the means for binding the front panel to the two side panels includes a lacing system using a wire strand wound around a rotating and ratcheting spool.

20. The orthopedic ankle brace of claim 16, wherein the at least two tendon buttresses include at least one of an ovoid shape, a rhomboid shape, and a tubular shape.

* * * * *